(12) United States Patent
Funane et al.

(10) Patent No.: US 10,548,518 B2
(45) Date of Patent: Feb. 4, 2020

(54) BIOPHOTONIC MEASUREMENT DEVICE AND METHOD

(71) Applicant: Hitachi, Ltd., Tokyo (JP)

(72) Inventors: Tsukasa Funane, Tokyo (JP); Takusige Katura, Tokyo (JP); Hirokazu Atsumori, Tokyo (JP); Masashi Kiguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 536 days.

(21) Appl. No.: 15/311,647

(22) PCT Filed: Jun. 23, 2014

(86) PCT No.: PCT/JP2014/066547
§ 371 (c)(1),
(2) Date: Nov. 16, 2016

(87) PCT Pub. No.: WO2015/198373
PCT Pub. Date: Dec. 30, 2015

(65) Prior Publication Data
US 2017/0079567 A1  Mar. 23, 2017

(51) Int. Cl.
*A61B 5/1455* (2006.01)
*A61B 5/00* (2006.01)

(52) U.S. Cl.
CPC ........ *A61B 5/14551* (2013.01); *A61B 5/7207* (2013.01); *A61B 5/7225* (2013.01); *A61B 5/742* (2013.01)

(58) Field of Classification Search
CPC . A61B 5/14551; A61B 5/7207; A61B 5/7221; A61B 5/7225; A61B 5/742; A61B 2562/046
See application file for complete search history.

(56) References Cited

U.S. PATENT DOCUMENTS 5,803,909 A    9/1998  Maki et al.
2005/0228291 A1 * 10/2005  Chance ............... A61B 5/0073
                                                    600/476
(Continued)

FOREIGN PATENT DOCUMENTS

JP      09-019408 A    1/1997
JP    2008-173140 A    7/2008
(Continued)

OTHER PUBLICATIONS

Smith, Chp 3, ADC and DAC, "The Scientist and Engineer's Guide to Digital Signal Processing", California Technical Publishing, 2011 (Year: 2011).*

(Continued)

*Primary Examiner* — Eric F Winakur
(74) *Attorney, Agent, or Firm* — Mattingly & Malur, PC

(57) ABSTRACT

In a biophotonic measurement device based on the principles of near-infrared spectroscopy (NIRS), in order to realize appropriate conditions in any light-source/detector arrangement and various required specifications, a photoirradiation module 13 including a light source 101, a photodetection module 14 including a photodetector 102, and a central control/analysis unit 18 are provided. The central control/analysis unit 18 acquires correspondence relations between each of photodetection units and photoirradiation units by using a correspondence acquiring unit 19. The photoirradiation module 13 and the photodetection module 14 switch signal detection methods at each measurement point by utilizing an evaluation function value determined by detection output of the photodetector 102 so that the plurality of signal detection methods are mixable, and the high-precision and optimum biophotonic measurement device is realized.

17 Claims, 13 Drawing Sheets

(56) References Cited

U.S. PATENT DOCUMENTS

| | | | |
|---|---|---|---|
| 2008/0234560 A1* | 9/2008 | Nomoto | A61B 5/14552 600/310 |
| 2008/0259337 A1 | 10/2008 | Sagara et al. | |
| 2009/0015839 A1* | 1/2009 | Kiguchi | A61B 5/1455 356/432 |
| 2012/0203088 A1* | 8/2012 | Tanii | A61B 5/0059 600/322 |

FOREIGN PATENT DOCUMENTS

| | | |
|---|---|---|
| JP | 2009-261588 A | 11/2009 |
| JP | 2011-024925 A | 2/2011 |

OTHER PUBLICATIONS

Sano et al., "ICA of Multi-channel NIR Spectroscopic Channels for Time-Delayed Decorrelation", ICANN, 2010, Part 1, LNCS 6352, pp. 511-520, 2010 (Year: 2010).*
Japanese Office Action received in corresponding Japanese Application No. 2017-187469 dated Apr. 17, 2018.
Atsushi Maki, et al., "Spatial and temporal analysis of human motor activity using noninvasive NIR topography", Medical Physics, Dec. 1995, pp. 1997-2005, vol. 22, No. 12.
International Search Report of PCT/JP2014/066547 dated Aug. 26, 2014.

* cited by examiner

BIOPHOTONIC MEASUREMENT DEVICE AND METHOD

TECHNICAL FIELD

The present invention relates to biophotonic measurement devices using visible light or near-infrared light and particularly relates to the techniques for measuring the oxygenated state biological-body tissues and hemodynamic changes in tissues.

BACKGROUND ART

Brain-function measurement devices using the principles of near-infrared spectroscopy (Near-infrared spectroscopy: NIRS) (see PTL 1, NPL 1) can be used as medical and research equipment or for checking educational effects and rehabilitation effects, health management at home, and market research such as commercial-product monitoring. Also, the devices can be used for tissue oxygen-saturation-degree measurement or oxygen metabolism measurement of muscle tissues by similar methods. Furthermore, the devices can be also used for general absorption spectroscopy apparatuses including sugar-content measurement of fruits.

Therefore, recently, demands for small light measurement devices such as during-exercise blood-flow monitors, saliva measurement, intraoperative brain oxygen monitors, etc. including brain-function measurement based on NIRS are increasing more and more. The specifications (wavelengths, the number of measurement points, sampling speed, etc.) of the small devices like these have to change measurement parts and the number of measurement channels (the number of measurement points) by depending on applications, and, conventionally, dedicated specifications had to be prepared for each of the applications. Therefore, it has been difficult to realize a module-type biophotonic measurement device for a common base, and it has been difficult to reduce the cost of the device supporting application of small NIRS, which are increasing more and more.

In such circumstances, PTL 2 discloses a method in which measurement regions and the number of channels can be freely set, detachable transmission/reception units are provided, and a main control unit adjusts timing by controlling a sub control unit of the attached transmission/reception unit to obtain measurement data about brain activities. Moreover, PTL 3 discloses a method in which, in order to realize a module-type photodetector which is detachable/attachable and excellent in safety, light receiver and light transmitter are made into modules, and, particularly in the light receiver, a high-voltage power source for driving a photodetector is housed in a package which can be fixed to the head.

CITATION LIST

Patent Literature

PTL 1: JP 09-019408 A
PTL 2: JP 2011-24925 A
PTL 3: JP 2008-173140 A

Non-Patent Literature

NPL 1: A. Maki et al., "Spatial and temporal analysis of human motor activity using noninvasive NIR topography", Medical Physics, Vol. 22, No. 12, pp. 1997-2005 (1995)

SUMMARY OF INVENTION

Technical Problem

However, in the conventional technique literatures such as above described PTL 3, acquisition of measurement data by controlling light sources and detectors disposed so as to realize set measurement regions and the number of channels has been disclosed. However, the points of mutually cooperating the light sources and the detectors, optimizing signal detection methods and photoirradiation power based on measurement conditions such as detection light volumes, detector arrangement, etc., and realizing appropriate measurement conditions with a high signal-to-noise ratio even in various required specifications have not been studied.

An object of the present invention is to provide biophotonic measurement devices and methods which enable mixing of a plurality of signal detection methods and realizes appropriate measurement conditions at a high signal-to-noise ratio even with respect to various light-source/detector arrangement or required specifications.

Solution to Problem

In order to achieve the above described object, the present invention provides a biophotonic measurement device including: a photoirradiation unit for radiating light to a photoirradiation point; a photodetection unit for detecting the light, which is radiated from the photoirradiation unit, at a photodetection point; and a processing unit configured to process detection output of the photodetection unit, wherein the processing unit sets a signal detection method between the photoirradiation unit and the photodetection unit by utilizing an evaluation function value determined by the detection output of the photodetection unit.

Moreover, in order to achieve the above described object, the present invention provides a biophotonic measurement method including: radiating light to a photoirradiation point from a photoirradiation unit; detecting the light, which is radiated from the photoirradiation unit by a photodetection unit, at a photodetection point; and switching a signal detection method between the photoirradiation unit and the photodetection unit by a processing unit by utilizing an evaluation function value determined by detection output of the photodetection unit.

Advantageous Effects of Invention

According to the present invention, highly precise biophotonic measurement is realized at a high signal-to-noise ratio since an optimum signal detection method can be selected in accordance with various conditions.

DESCRIPTION OF EMBODIMENTS

Hereinafter, embodiments of the present invention will be described by using drawings. In different drawings, configuration blocks and configuration elements represented by the same numbers represent the same objects. As described below, in preferred modes of the present invention, a biophotonic measurement device supporting required specifications is formed by combining light-source/detector/control measurement modules, and signal detection methods can be dynamically optimized in accordance with circumstances such as a human subject, part, tasks (cognitive task), etc.

First Embodiment

A first embodiment is an embodiment of a biophotonic measurement device including: a photoirradiation unit for radiating light to a photoirradiation point; a photodetection unit for detecting the light, which is radiated from the photoirradiation unit, at a photodetection point; and a processing unit which processes detection output of the photodetection unit, wherein the processing unit is configured to switch signal detection methods between the photoirradiation unit and the photodetection unit by utilizing evaluation function values determined by the detection output of the photodetection unit.

Figure 1:
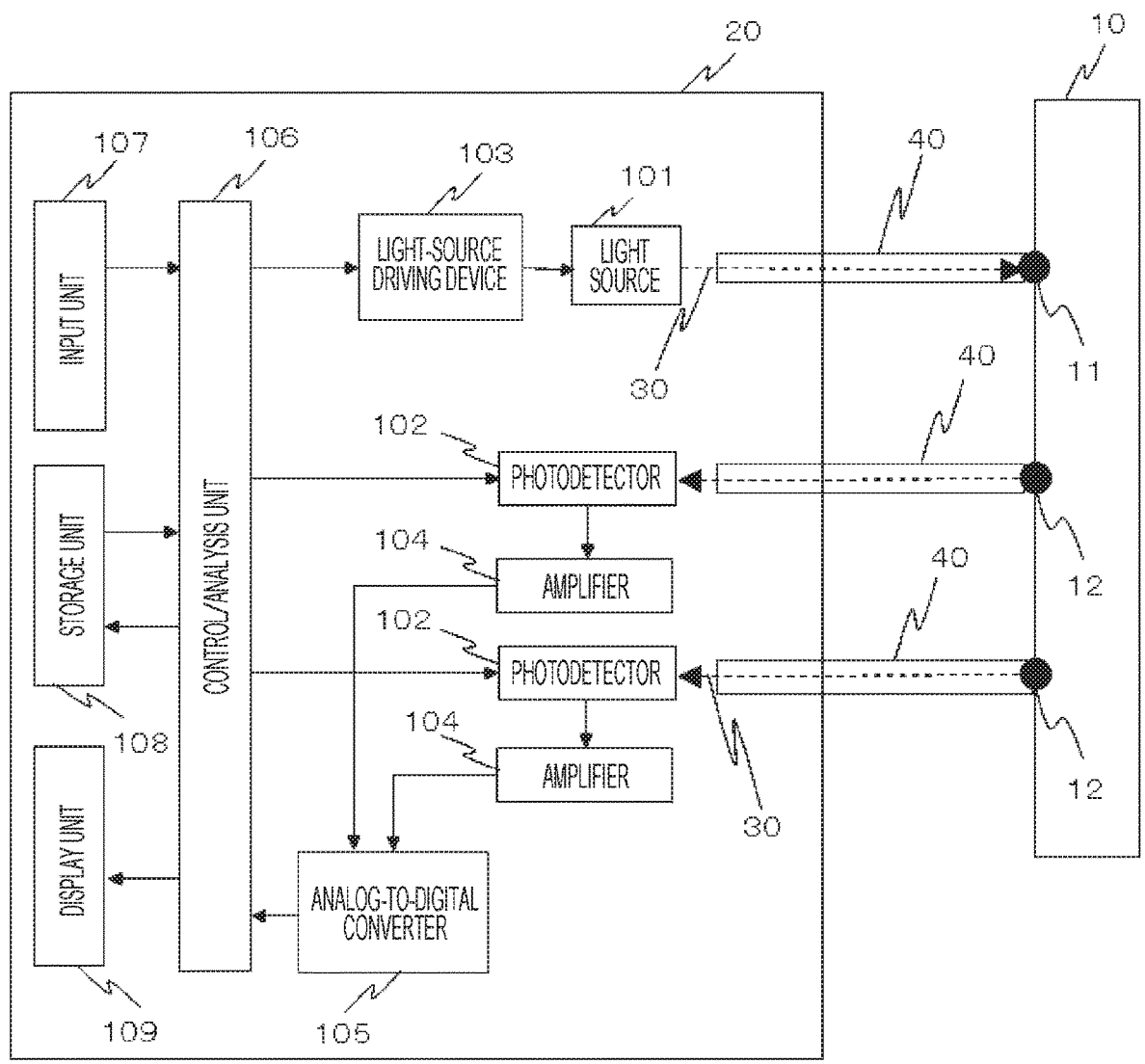
FIG. 1 shows an example of an overall configuration of a biophotonic measurement device of a first embodiment.

FIG. 1 shows an example of an overall configuration of a biophotonic measurement device of the present embodiment. In the biophotonic measurement device capable of injecting light into a biological body and detecting the light scattered/absorbed and propagated in the biological body and released to outside the biological body, light 30 radiated from a light source(s) 101, which is one or a plurality of photoirradiation units included in a chassis 20, is injected to an irradiation point of a human subject 10 via a waveguide 40 for propagating light. The light 30 from the photoirradiation unit(s) is injected into the human subject 10 from the irradiation point 11, is transmitted and propagated in the human subject 10, and is then detected by a photodetector(s) 102, which is one or a plurality of photodetection units, from a detection point(s) 12, which is at a position(s) distant from the irradiation point 11, via a waveguide(s) 40 constituting a probe(s). Therefore, the irradiation-detector (source-detector) distance (SD distance) is defined by the distance between the irradiation point 11 and the detection point 12.

Herein, the one or plurality of light sources 101 may be a semiconductor laser (LD), a light-emitting diode (LED), or the like, and the one or plurality of photodetector 102 may be an avalanche photodiode (APD), a photodiode (PD), a silicon photomultiplier (SiPM), a photomultiplier tube (PMT), or the like. The waveguide 40 constituting the probe may be a medium such as optical fibers, glass, a light guide, or the like through which used wavelengths can propagate through.

The light source 101 is driven by a light-source driving device 103, which is in the chassis 20, and the multiplication factor and gain of the one or plurality of photodetectors 102 are controlled by a control/analysis unit 106, which is a processing unit. The control/analysis unit 106 also controls the light-source driving device 103 and receives input of conditions, etc. by an operator from an input unit 107. Electric signals obtained by carrying out photoelectric conversion in the photodetector 102 are amplified by an amplifier 104, are subjected to analog-to-digital conversion in an analog-to-digital converter 105, and transmitted to the control/analysis unit 106, which is the processing unit, and are subjected to signal processing.

The methods of detecting minute signals and separating a plurality of signals using the light source 101, which is the photoirradiation unit, and the photodetector 102, which is the photodetection unit, include a method of driving the plurality of light sources by an intensity modulating method and subjecting the signals detected by the photodetectors to lock-in detection and then to analog-to-digital conversion and include a method of subjecting the signals from a light receiver to amplification/analog-to-digital conversion and then digitally carrying out lock-in processing. The methods are not limited thereto. For example, a time-division detection method in which a plurality of rays of light is discriminated by shifting the timing to radiate the plurality of rays of light in terms of time and a spread spectrum modulation method can be also used.

Note that the light source 101, which is the photoirradiation unit, and the photodetector 102, which is the photodetection unit, may be configured to be integrated with the waveguide 40. For example, if a light-source element such as LD, LED, or the like and a photodetection element such as PD, APD, or the like are installed in the probe, there are effects such as reduction of light loss, downsizing of the device, reduction of cost, and reduction of consumed electric power.

In the control/analysis unit 106, which is the processing unit, analysis is executed based on detection output detected by the photodetector 102. Specifically, digital signals obtained by conversion in the analog-to-digital converter 105 are received, and, based on the digital signals, for example, based on a method described in NPL 1, oxygenated (oxygenated hemoglobin: oxy-Hb) and deoxygenated hemoglobin changes (deoxygenated hemoglobin: deoxy-Hb) are calculated from detection light volume changes or absorbance changes. The oxygenated and deoxygenated hemoglobin changes are the values corresponding to the amounts of changes in the product of a hemoglobin concentration and an effective light-path length. Alternatively, the amounts of changes in the hemoglobin concentration may be calculated by assuming an appropriate light-path length and using it for substitution.

Herein, the description is given on the assumption that the control/analysis unit 106, which is the processing unit, carries out all of driving of the light source(s) 101, gain control of the photodetectors 102, and processing of the signals from the analog-to-digital converter 105. However, the same function can be realized by providing separate control units, respectively, and providing a means to integrate them. Meanwhile, measurement data and the calculation results of hemoglobin changes are saved in a storage unit 108, and measurement results can be displayed by a display unit 309 based on analysis results and/or the saved data. The control/analysis unit 106, the input unit 107, the storage unit 108, and the display unit 309 can be formed by using, for example, an information terminal or the like composed of at least one personal computer (PC).

Regarding a light transmitter and a light receiver omitted in illustration in FIG. 1, the light transmitter includes, for example, the waveguide 40 of the light source 101 side and is installed in a state in which the light transmitter is in contact with or is nearly in contact with the human subject 10, and the light receiver includes, for example, the waveguide 40 of the photodetector 102 side and is installed in a state in which the light receiver is in contact with or is nearly in contact with the human subject 10.

In a preferred mode of the biophotonic measurement device of the present embodiment, part or all of the above described configurations is made into a module(s), and blood volume changes of human tissues or the amounts of hemoglobin changes are measured with the single or plurality of modules. In other words, this shows a configuration of a biophotonic measurement device having: one or a plurality of photoirradiation units for radiating light to a predetermined photoirradiation point; one or a plurality of photodetection units for detecting the light, which is radiated from the photoirradiation unit, at a predetermined photodetection point; one or a plurality of optical device modules for storing at least one of the photoirradiation unit and the photodetection unit; and a correspondence acquiring unit for acquiring a correspondence relation between each of the photodetection unit and the photoirradiation unit predetermined, which is an irradiation source of the light detected by the detection unit, wherein the optical device module has an information storage unit storing information about at least one of the photoirradiation unit and the photodetection unit and has a control communication unit for controlling at least one of the photoirradiation unit and the photodetection step and communicating with another optical device module; signal detection methods are switched among the optical device modules by utilizing the correspondence relation and the detection intensity of the photodetection unit or an evaluation function value determined by the detection intensity and measurement conditions so that the plurality of signal detection methods are mixable at measurement points.

Figure 2:
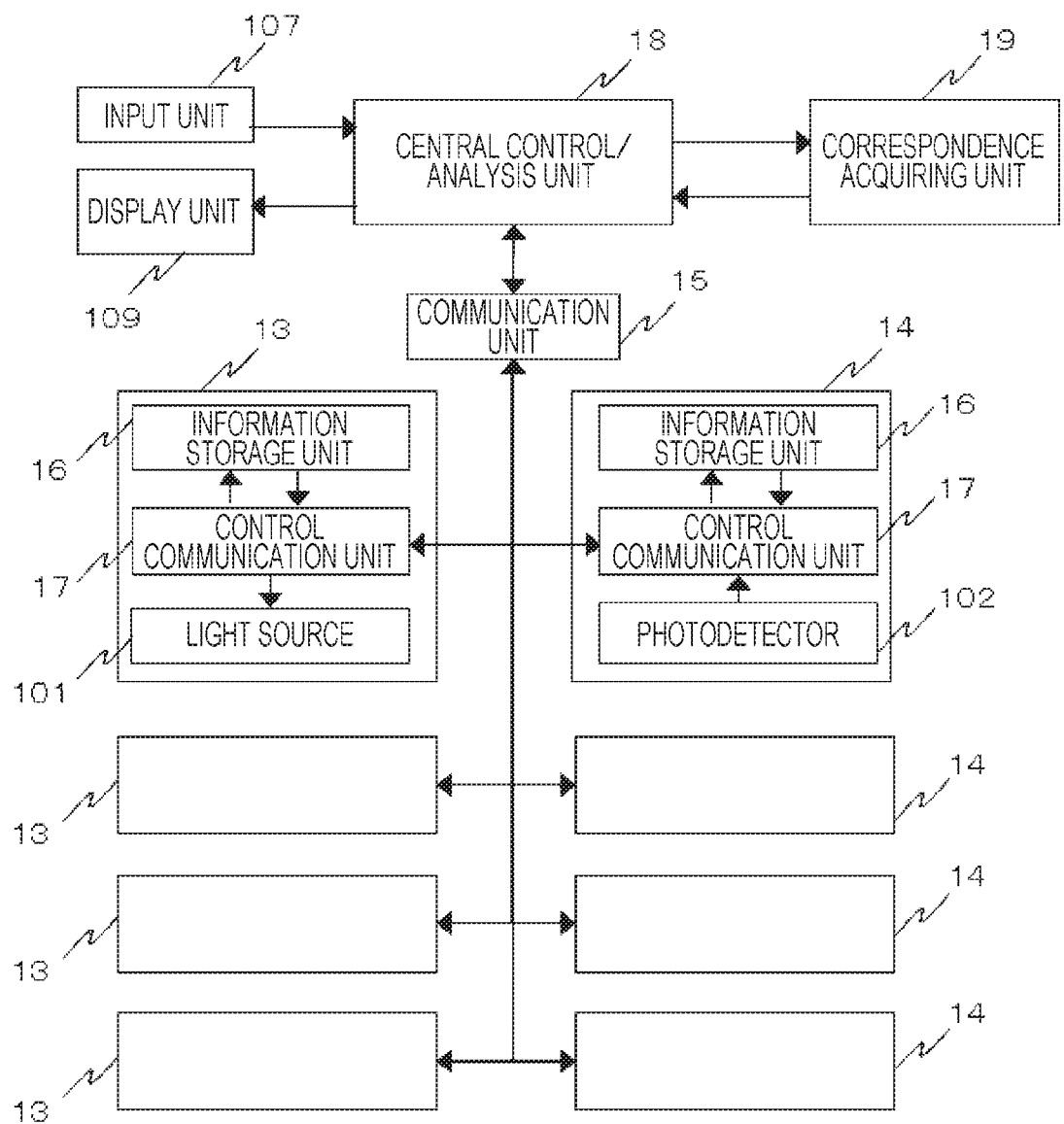
FIG. 2 is a view showing an example of the biophotonic measurement device according to the first embodiment formed by modules.

FIG. 2 is a preferred configuration example of the biophotonic measurement device of the present embodiment formed by this module building. This module building is realized by using a plurality of photoirradiation modules and photodetection modules 14. The photoirradiation module 13 includes, in the interior thereof, the light source 101, which is a photoirradiation unit, an information storage unit 16, and a control communication unit 17; and information of the light source 101 including wavelengths, photoirradiation intensity, modulation methods, parameters of the modulation method, etc. is retained in the information storage unit 16. Herein, the modulation methods are the above described continuous digital lock-in method, a continuous analog lock-in method, a time-division detection method, a code division modulation method, etc. The parameters of the modulation methods are the parameters of the modulation methods such as frequencies, pulse widths, code waveforms, cycles, etc.

Meanwhile, the photodetection module 14 includes, in the interior thereof, the photodetector 102, which is the photodetection unit, an information storage unit 16, and a control communication unit 17. The information storage unit 16 retains information of the photodetector 102 such as current-light output characteristics, light reception sensitivity, a maximum sensitivity wavelength, dark currents, inter-terminal capacities, etc. The photoirradiation module 13 and the photodetection module 14 have the control communication units 17 and communicate with another module or a central control/analysis unit 18 via the communication unit 15.

The central control/analysis unit 18, which is a processing unit, corresponds to the control/analysis unit 106 shown in FIG. 1 and includes a correspondence acquiring unit 19 as a functional block. Furthermore, as well as FIG. 1, the configuration of FIG. 2 has the input unit 107 for manually or automatically inputting various parameters and the display unit 309 for displaying the results after correspondence acquisition by the correspondence acquiring unit 19, measurement results, etc.

The correspondence acquiring unit 19 is realized by program execution or the like by the central control/analysis unit 18 and, based on the information from the photoirradiation module 13 and the photodetection module 14, acquires the correspondence relations between the photoirradiation modules 13 and the photodetection modules 14, in other words, the information that which photodetection module detects the light radiated from which photoirradiation module 13 and acquires signals. Furthermore, as this correspondence relation, the correspondence acquiring unit 19 may acquire the SD distance defined by the distance between the irradiation point 11 of light and the detection point 12. Also, modules may be installed for standard phantoms (biological-body tissue stimulant materials) or human subjects, combinations of time-average detection light volumes or signal-to-noise ratios (signal-to-noise ratio: SNR) of the cases in which the light source 101 is lit and the output of the photodetector 102 may be acquired, and the above described correspondence relations may be defined or acquired when the values thereof are equal to or higher than a predetermined threshold value.

Figure 3:
FIG. 3 is a view showing examples of photodetection waveforms in various signal detection methods according to the first embodiment.
Figure 3:
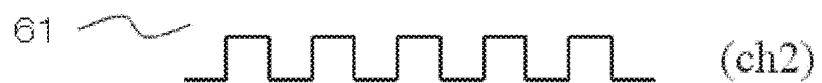
Figure 3:
Figure 3:
Figure 3:
Figure 3:
Figure 3:
Figure 3:
Figure 3:
Figure 3:
Figure 3:
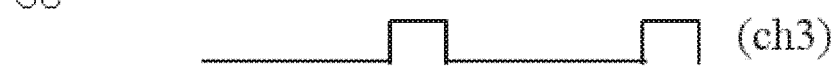

FIG. 3 shows an example of photodetection waveforms in various signal detection methods used by the biophotonic measurement device of the present embodiment. Each of the waveforms represents an example of a raw waveform of a photodetection signal. Photodetection waveforms (ch 1, 2) of the continuous light lock-in method are represented by 61. An intensity modulation signal can be decoded by multiplying (multiplying) a light signal, which has been subjected to intensity modulation by a predetermined frequency, by a reference signal of the same frequency in the same phase. A photodetection waveform of a quasi continuous light lock-in method is represented by 62. If there is no usage of another light signal, this method is similar to the continuous light lock-in method. However, if there is usage of another light signal of photodetection signals, this method turns off the signal at the timing when the other light signal starts lighting so as to avoid interference with the other light signal and does not carry out computation processing of lock-in detection in that period. Photodetection waveforms (ch 1 to 3) of a time-division lock-in method are represented by 63. This method sequentially carries out lighting in order to reduce interference between light sources in a case in which the plurality of light sources is used, and this method carries out intensity modulation at a frequency higher than a switch frequency in order to reduce noise of interior illumination, etc. Photodetection waveforms (ch 1, 2) of a lock-in switch method are represented by 66, and this method alternately switches two types of light source sets and is a special case of the time-division lock-in method. Photodetection waveforms (ch 1 to 3) of the time-division detection method are represented by 68, and this method sequentially lights a plurality of light sources.

These various modulation methods are known to have advantages/disadvantages particularly when the number of measurement channels is large or small. For example, if the number of measurement channels is large, in a time-division method including the time-division lock-in method, time is taken for one cycle, the measurement time per one channel has to be reduced in order to maintain temporal resolution; and, if the measurement time is maintained, the temporal resolution is reduced. In the continuous light lock-in method, if light sources are not concentrated on a single detector, for example, if a normal grid-shaped arrangement is used, such a problem is not caused.

However, if many (for example, 6 or more) light sources are allocated to a single detector, in the continuous light lock-in method, average light reception power is increased, shot noise due to photocurrents of the detector may be increased, and the detector may be saturated and disable measurement per se. Therefore, if many light sources are allocated to a single detector in this manner, the time-division lock-in method or another time-division detection method is more suitable. Furthermore, in order to obtain high signal-to-noise ratios at more measurement points, the irradiation power of the light sources may be changed, and the amplification factors of photodetectors may be changed. The amplification factor of the photodetector can be realized by, for example, changing a feedback resistance value of an amplifier in a detection system circuit or a circuit parameter such as an input resistance value. The above description has been described as examples. In actual measurement, regardless of the arrangement or used number of light sources and detectors, an optimum detection method may be changed depending on the transmittance of the subject 10, used wavelengths, environments of electromagnetic and mechanical noise therearound, etc.

Figure 4:
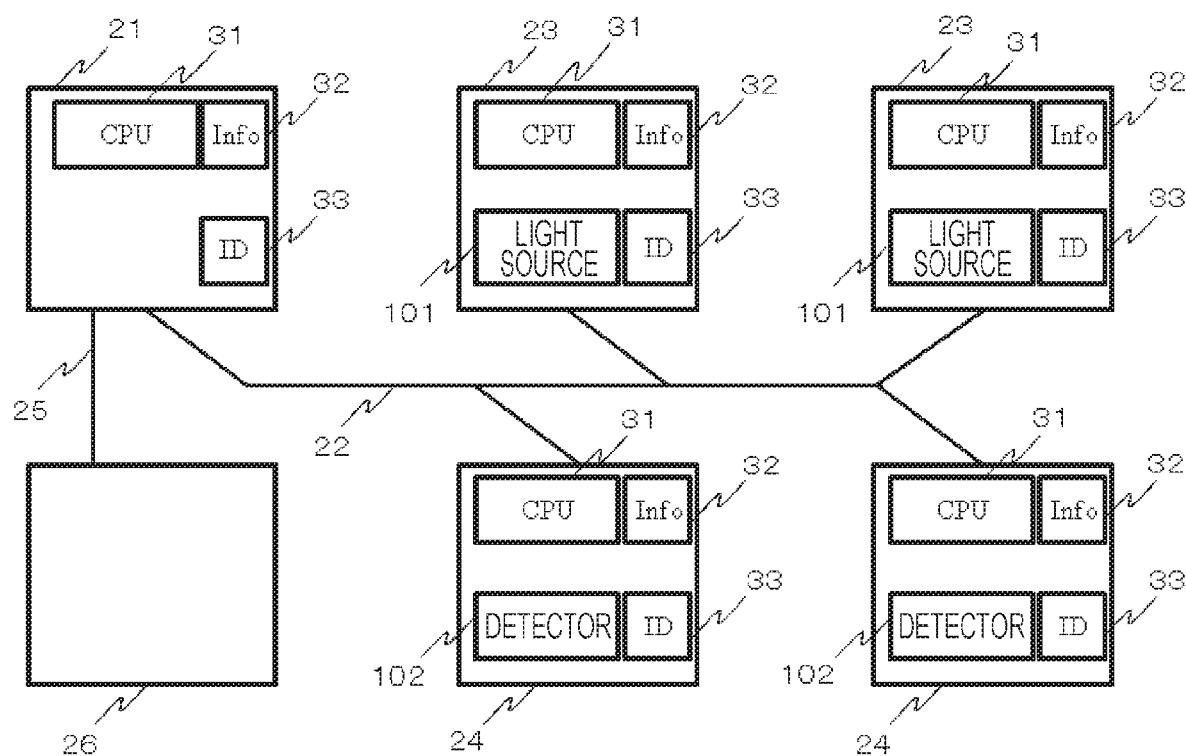
FIG. 4 shows an example of the biophotonic measurement device formed by a plurality of optical device modules and control modules according to the first embodiment.

Another example of the configuration of module building of the biophotonic measurement device of the present embodiment will be described by using FIG. 4. FIG. 4 shows an example of the biophotonic measurement device formed by a plurality of optical modules and control modules. A control module 21, photoirradiation modules 23, and photodetection modules 24 are mutually communicated via an inter-module communication bus 22. Each of the modules has module information 32, a module ID 33, a central computation processing unit (CPU) and a storage unit 31. For optical measurement, the photoirradiation module 23 includes the light source 101, which is a photoirradiation unit, and the photodetection module 24 includes the photodetector 102, which is a photodetection unit.

Note that each of the modules includes a communication connector, etc. as a control communication unit in the configuration of FIG. 2. However, illustration thereof is omitted in FIG. 4. The control module 21 is controlled from an information terminal 26 via a communication bus 25 between the module and the information terminal. The control module 21 and the information terminal 26 correspond to the control/analysis unit 106, the input unit 107, the storage unit 108, and the display unit 309 of the configuration of FIG. 1. Note that, as the CPU and storage unit 31 of the module like this, a FPGA (Field-Programmable Gate Array), a PSoC (registered tradename: Programmable System-on-Chip), or the like can be utilized.

Figure 5:
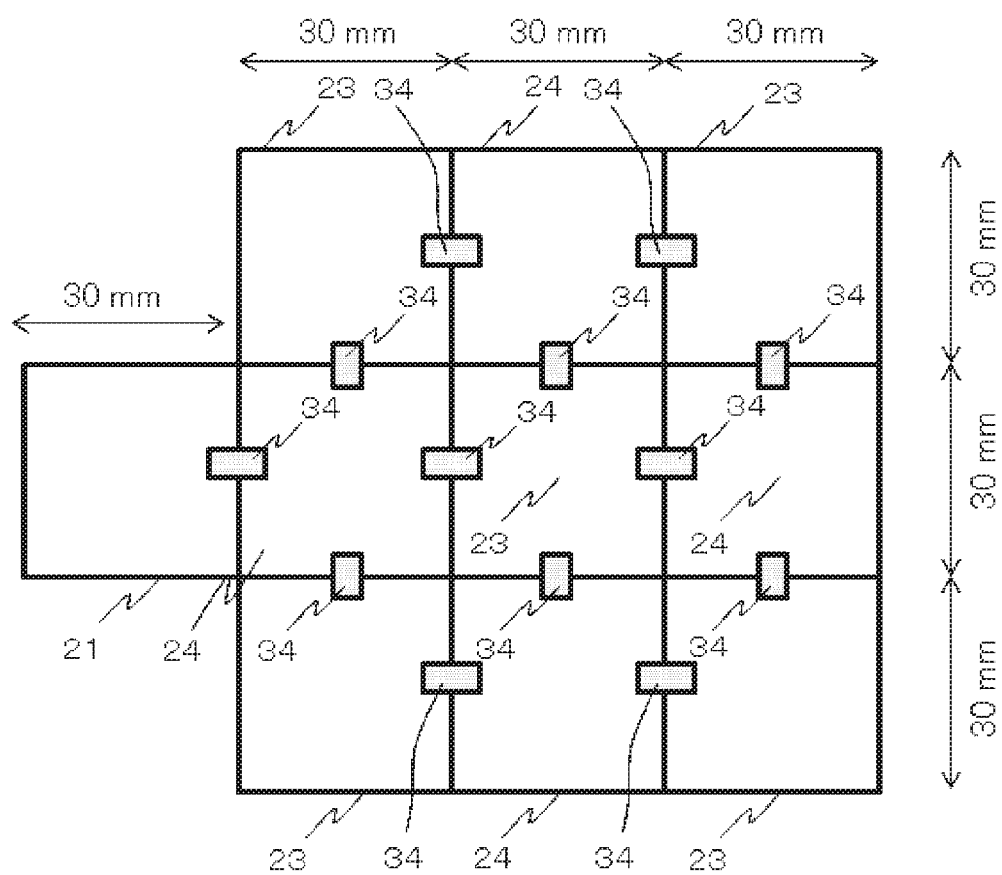
FIG. 5 is a view showing an example of a module arrangement of the biophotonic measurement device according to the first embodiment.

Next, FIG. 5 is a view showing an example of a module arrangement of a case in which the plurality of modules shown in FIG. 4 is installed for the subject 10. Herein, the distance between irradiation-detector is set to 30 mm. The photoirradiation modules 23 and the photodetection modules 24 are alternately disposed with inter-module connectors 34 provided between the modules, and "3×3 arrangement" (in total 9 modules are arranged like a grid in 3 rows and 3 columns) is realized. Furthermore, the control module 21 is separately disposed.

Figure 6:
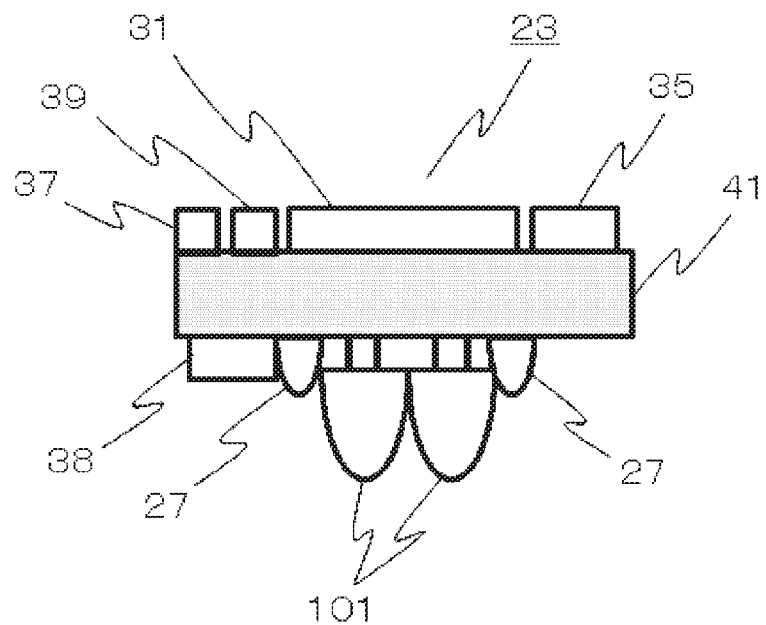
FIG. 6 is a view showing an example of a photoirradiation module configuration according to the first embodiment.

Subsequently, by using FIG. 6 to FIG. 8, examples of a device configuration of the plurality of modules shown in FIG. 4 and FIG. 5 are shown. FIG. 6 is a view showing an example of the device configuration of the photoirradiation module 13. On a substrate 41, light sources 101, monitor photodetectors 27, the central computation processing unit (CPU) and storage unit 31, a connector 38 for communication with the information terminal, a firmware-writing connector 35, a connector 37 for communication between the modules, and a power source 39 are installed. As the central computation processing device (CPU) and storage unit 31, one that can implement embedded software or firmware may be used, furthermore, one that can dynamically change an internal hardware configuration may be used, and PSoC (registered tradename) described before, a microcontroller, or the like may be used.

As the light sources 101, light-emitting diodes (LED) or the like may be used. Since 2 wavelengths are used, 2 LEDs are installed. Meanwhile, the monitor photodetectors 27 for measuring the irradiation intensities of the respective LEDs, which can be changed by ambient temperatures, may be normal photodiodes (PD), are disposed in the vicinities of the respective LEDs 101, and are disposed so as to reduce the influence of the light of the other LED. For example, at the positions point-symmetric to the center of a line segment of a case in which the installation positions of the 2 LEDs 101 are connected to each other by a straight line, the 2 monitor photodetectors 27 may be disposed on the straight line. For example, it is assumed that the present module is used for measurement of a human head, that a grid-like probe arrangement is used, and that the distance between the respective light sources 101 and the photodetectors 102 is set to 30 mm; and, herein, the substrate 41 has a square shape, and the light sources 101 are disposed at the center of the substrate. By virtue of this, as a result of arranging the substrates in a grid arrangement, a grid-like arrangement of the light sources and photodetectors can be realized.

Figure 7:
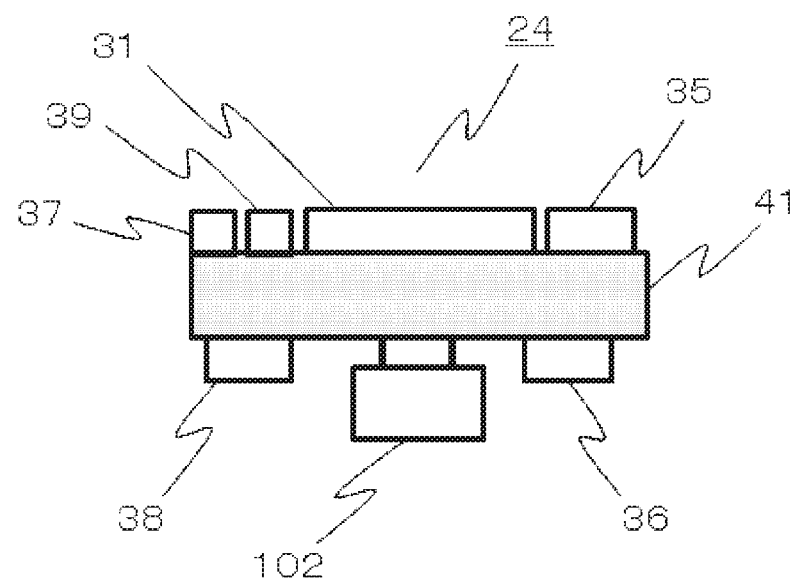
FIG. 7 is a view showing an example of a photodetection module configuration according to the first embodiment.

FIG. 7 is a view showing an example of the configuration of the photodetection module 24. On the substrate 41, the photodetector 102, the amplifier 36 for amplifying detected light signals, the connector 37 for communication between the modules, the connector 38 for communication with the information terminal, the firmware-writing connector 35, the central computation processing device (CPU) and storage unit 31, and the power source 39 are disposed. As well as the photoirradiation module 23, also in the photodetection module 14, a grid-shaped probe arrangement can be easily realized in human head measurement by installing the photodetector 102 in the vicinity of the center of the substrate 41 and arranging the substrates in a grid arrangement.

Note that, if the photoirradiation module 23 and the photodetection module 24 are collectively defined as optical device modules, the optical device module stores the information about at least one of the light sources 101 and the photodetector 102, controls at least one of the light sources 101 and the photodetector 102, and has the CPU and storage unit 31 for communicating with another optical device module. In a preferred mode of the present embodiment, as described later in detail, in accordance with the detection intensity or measurement conditions of the signals which are the detection output of the light source 101 and the photodetector 102, the signal detection methods can be switched among the optical device modules, and the plurality of signal detection methods is configured to be mixable at measurement points.

Figure 8:
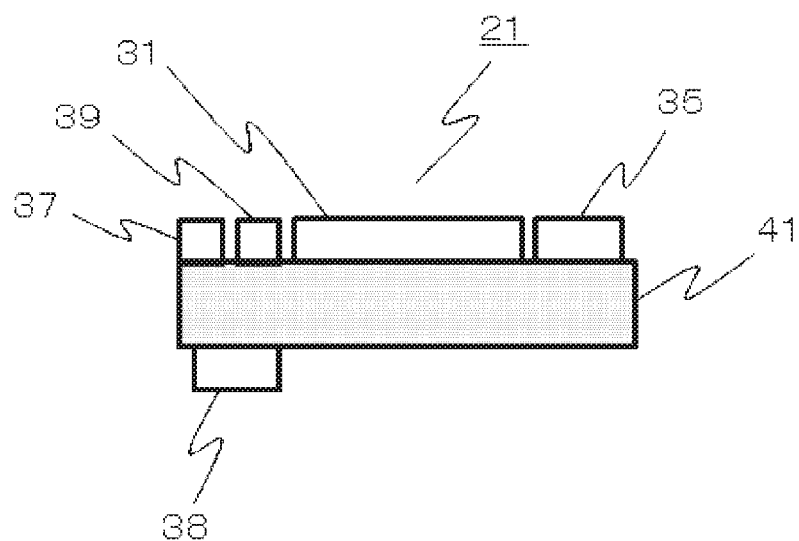
FIG. 8 is a view showing an example of a control module configuration according to the first embodiment.

FIG. 8 is a view showing an example of the device configuration of the control module 21. On the substrate 41, the CPU and storage unit 31, the firmware-writing connector 35, the connector 37 for communication between the modules, the connector 38 for communication with the information terminal, and the power source 39 are installed. In the configuration of the biophotonic measurement device using a plurality of modules, the control module 21 mainly functions as a master in the communication between the modules and controls the one or plurality of photoirradiation modules 23 and the one or plurality of photodetection modules 24. Furthermore, the control module 21 carries out communication with the information terminal 26 and carries out data output to the information terminal 26 and data input from the information terminal 26. Herein, the information terminal 26 may be a PC, a portable/mobile terminal, or the like as described above.

Figure 9:
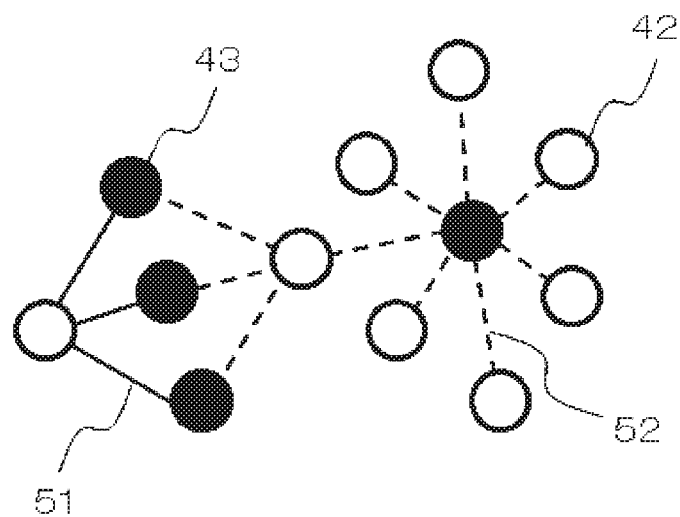
FIG. 9 is a view showing an example of a probe arrangement according to the first embodiment.

FIG. 9 shows an example of a probe arrangement of the present embodiment. Positions 42 of the light sources, which are the photoirradiation units, are shown by white circles, and positions 43 of the photodetectors, which are the photodetection units, are shown by black circles. As the lines connecting the light-source positions 42 and the photodetector positions 43, solid lines represent lines 51 showing the combinations of the light sources and the photodetectors which carry out the quasi continuous light measurement, and dotted lines represent lines 52 showing the combinations of the light sources and the photodetectors which carry out the time-division lock-in measurement. The part in which quasi continuous light measurement is carried out is a region in which the number of light sources is small and is not easily saturated even when light is continuously received; therefore, the light reception power per each light source can be increased, and the quality of signals can be enhanced. The part in which time-division lock-in measurement is carried out is a region in which the number of the light sources is large (herein, 7) with respect to the photodetector, wherein, in a continuous lock-in measurement method or a quasi continuous lock-in measurement method, the detector is easily saturated, and shot noise due to photocurrents is increased. Therefore, herein, the saturation and shot-noise increase of the detector is configured to be prevented by using the time-division lock-in method so that the signals from the necessary light sources can be subjected to light reception.

Figure 10:
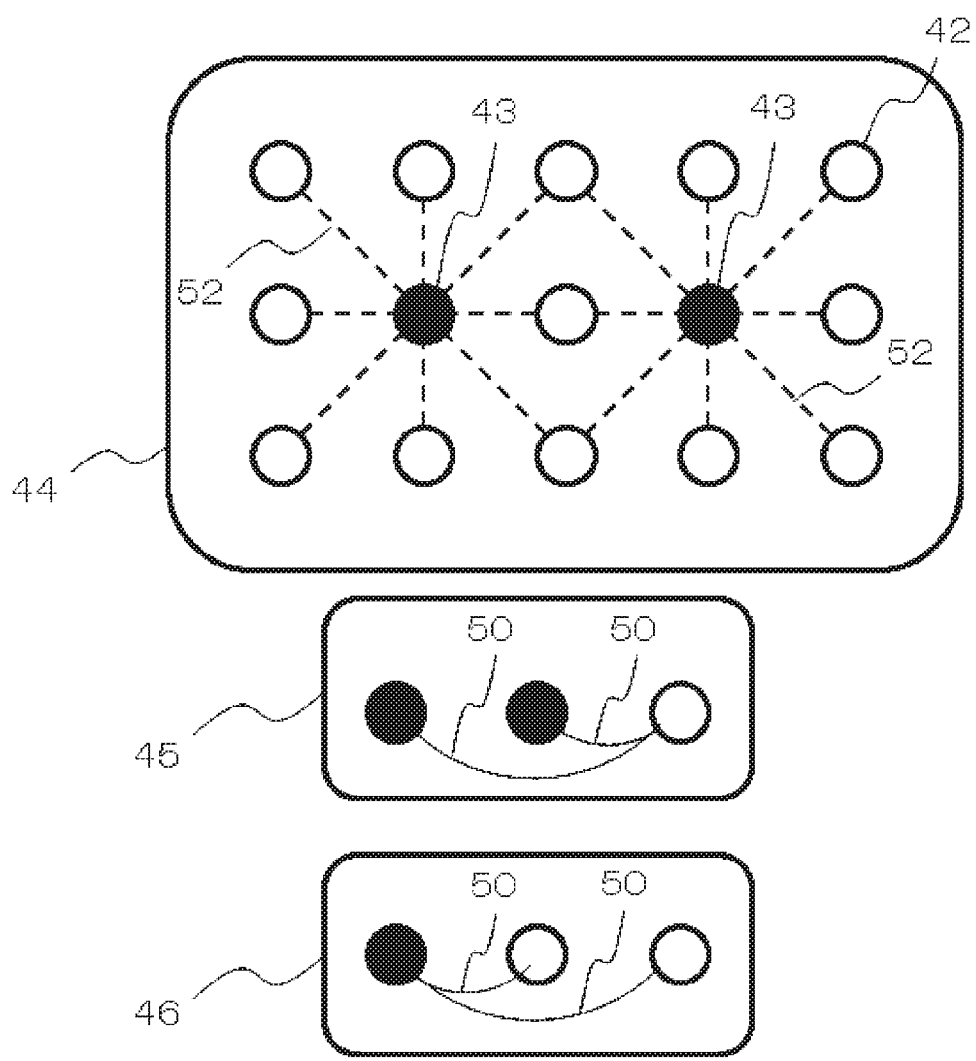
FIG. 10 shows probe holders and probe arrangement examples for simultaneously measuring a plurality of regions according to the first embodiment.

FIG. 10 shows a probe holder and a probe arrangement example for simultaneously measuring a plurality of regions of the biophotonic measurement device of the present embodiment. As well as FIG. 9, as the lines connecting the light-source positions 42 and the photodetector positions 43, solid lines represent lines 51 showing the combinations of the light sources and the photodetectors which carry out continuous light lock-in measurement, and dotted lines represent lines 52 showing the combinations of the light sources and the photodetectors which carry out the time-division lock-in measurement. If the plurality of regions is assumed to be regions A, B, and C herein, since the number of the light sources 101 with respect to the single photodetector 102 is 8 in the probe holder 44 installed in the region A, time-division lock-in measurement is configured to be carried out. Since the number of the light sources 101 with respect to the single photodetector 102 is small in a probe holder 45 installed in the region B and a probe holder 46 installed in the region C, continuous light lock-in measurement is configured to be carried out.

Subsequently, a method of setting an evaluation function value for quantitatively evaluating the quality of the detection signal, which is the detection output, and selecting an optimum signal detection method on condition that it reaches a predetermined standard in the biophotonic measurement device of the present embodiment will be described. First, the correspondence acquiring unit 19 of FIG. 2 carries out correspondence acquisition of the light sources and the detectors in accordance with the flow chart of FIG. 11. More specifically, the correspondence acquiring unit 19 carries out steps S111 to S115 of the flow chart of FIG. 11 and can be realized by software, firmware, hardware in the CPU and storage unit 31.

Figure 11:
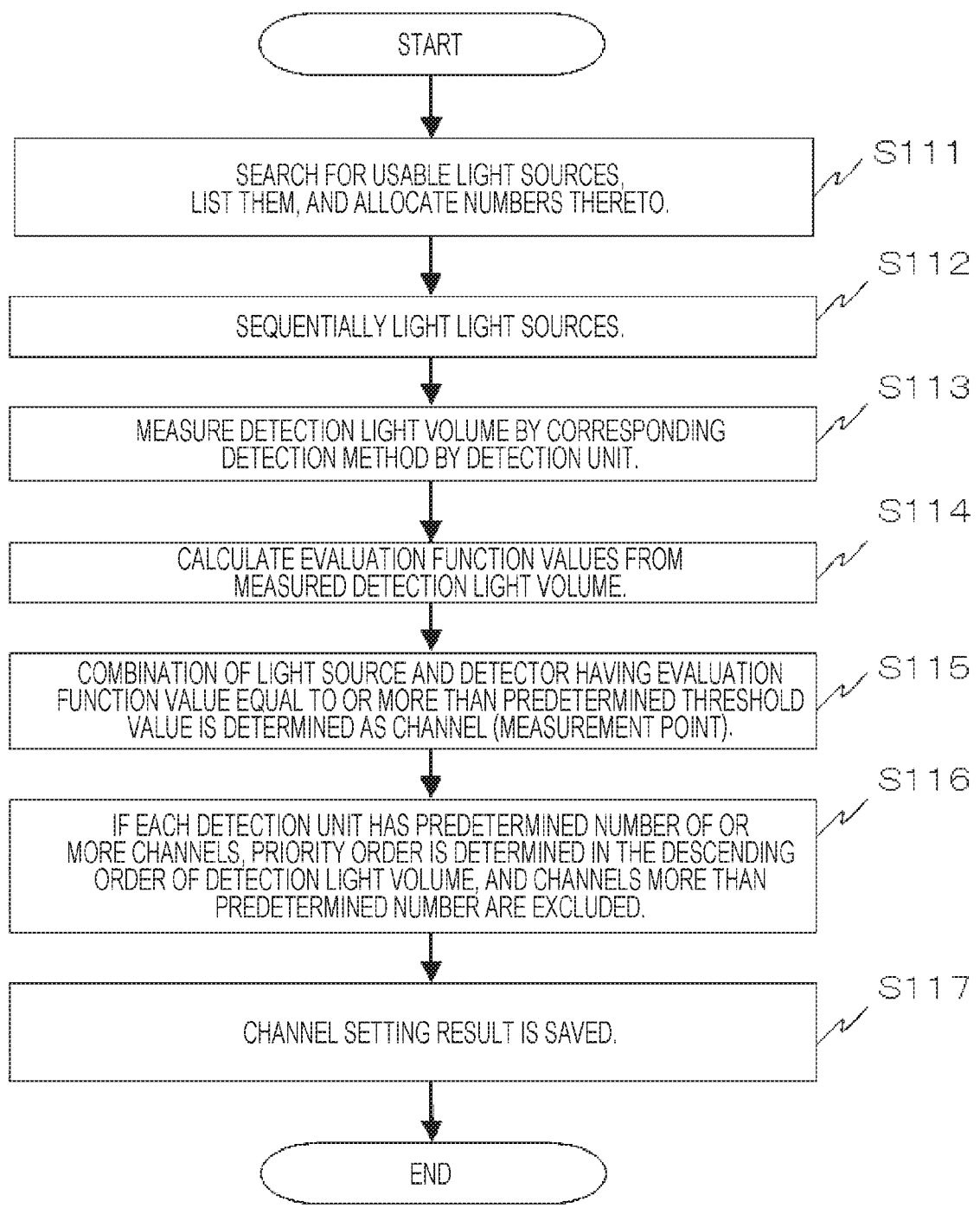
FIG. 11 is a view showing a flow chart in a case of correspondence acquisition of light sources and detectors according to the first embodiment.

In FIG. 11, first, the usable light sources, which are the photoirradiation units, are searched for and listed, and numbers are allocated thereto (step S111). The search of the light sources may be the search of the information of the connected light sources from inter-module communication through the inter-module communication bus 22, etc. or may be carried out by manual input. Then, the light sources are sequentially lit (step S112), detection light volumes are measured by the photodetectors, which are the photodetection units, by the corresponding signal detection methods (step S113), and evaluation function values are calculated (step S114). Then, the combinations of the light sources and the detectors having the evaluation function values equal to or higher than a predetermined threshold value are determined as channels (measurement points) (step S115). More specifically, the combinations of the usable light sources 101 and the photodetectors 102 are acquired.

If each of the photodetector has the channels equal to or higher than a predetermined number, a priority order is determined in the descending order of the detection light volumes or the evaluation function values, and the channels exceeding the predetermined number are excluded (step S116). As a method in which the predetermined number is not set, a method in which, when the number of the light sources is increased, at the point when a predetermined signal-to-noise ratio or less is obtained, the channel which is the cause thereof is excluded may be also used. A case in which the channels are not desired to be increased more than the predetermined number so as not to reduce temporal resolution is conceivable. Therefore, in that case, used channels may be set so that the temporal resolution does not become equal to or less than the temporal resolution input in advance. In the end, the channel setting result is saved in the storage unit 18 (step S117). Herein, a method in which a predetermined signal-to-noise ratio is ensured by changing the photoirradiation power of each light source may be also used. For example, a method which reduces photoirradiation power if the detection light volume is too strong and increases the photoirradiation power if the detection light volume is too weak is conceivable.

Note that the evaluation function in the present embodiment refers to a function which determines the quality of a signal. As the evaluation function value, for example, a carrier-to-noise ratio (carrier-to-noise ratio: CNR) expressed by Mathematical Expression 1, a signal-to-noise ratio (signal-to-noise ratio: SNR) expressed by Mathematical Expression 2, or the like may be used.

[Mathematical Expression 1]

$$CNR = 20\log_{10}\frac{mean(V)}{std(V)},$$  Mathematical Expression 1

Herein, mean (V) represents an average value of detection-light-volume time-series data of a predetermined wavelength in a predetermined period, and std (V) represents a standard deviation of the detection-light-volume time-series data of the predetermined wavelength in the predetermined period.

[Mathematical Expression 2]

$$SNR = 20\log_{10}\frac{mean(\Delta C_{Hb})}{std(\Delta C_{Hb})},$$  Mathematical Expression 2

Herein, mean($\Delta C_{Hb}$) represents an average value of hemoglobin-change time-series data in a predetermined period, and std($\Delta C_{Hb}$) represents a standard deviation of the hemoglobin-change time-series data in the predetermined period.

For example, sequential lighting is carried out for a predetermined period, the signals from the light sources, which are all the photoirradiation units, are detected by the photodetectors, which are all the photodetection units, detection intensity is recorded, and the evaluation function values representing the quality of the signals are calculated. As a result, when each of the evaluation function values exceeds the predetermined threshold value, it is determined as the correspondence relation for which signals are acquired. Note that, instead of using this method, the correspondence may be acquired by manual input from the input unit 107.

Figure 12:
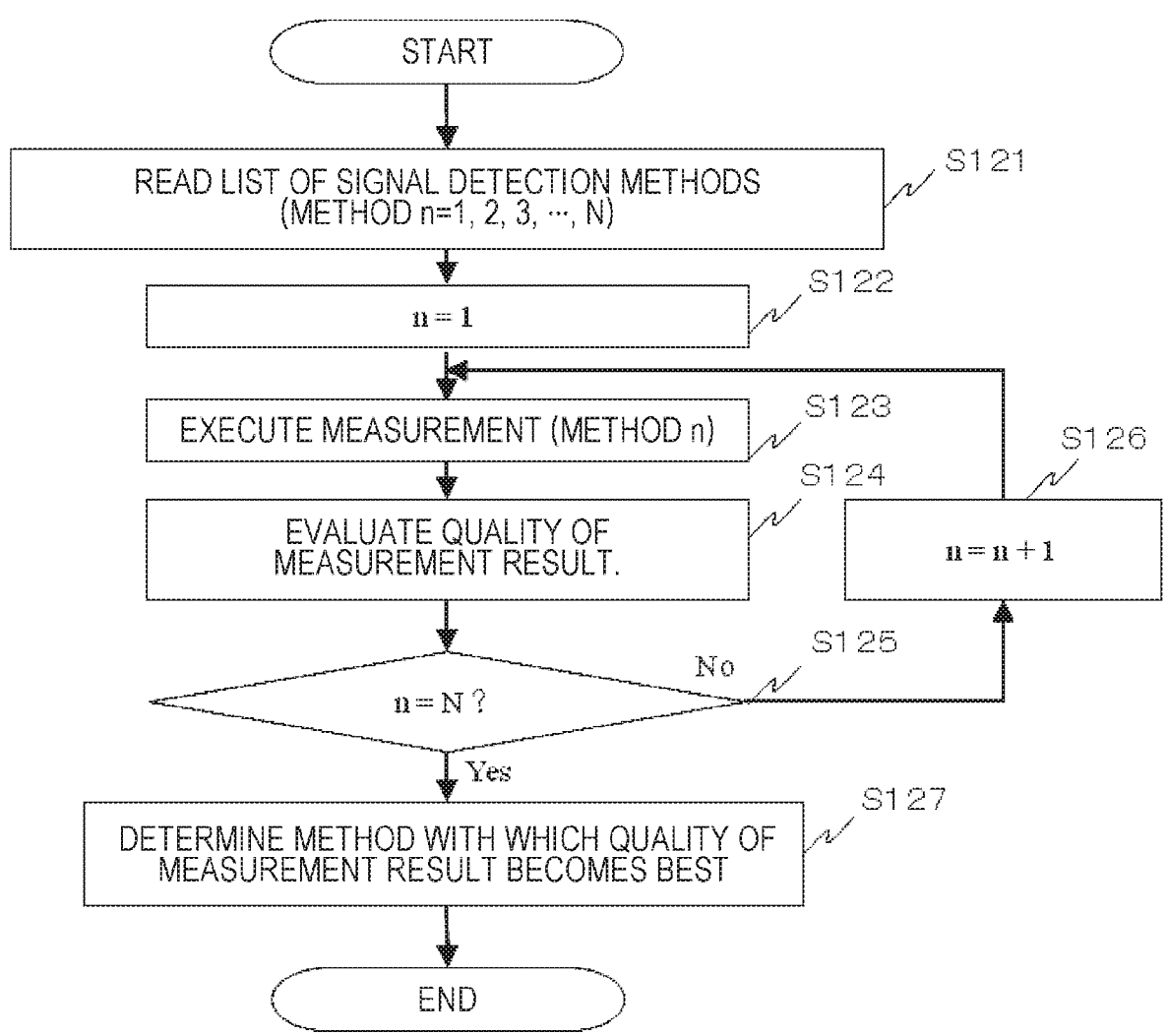
FIG. 12 is a view showing a flow chart in a case of acquisition of signal detection methods according to the first embodiment.

FIG. 12 is a view showing a flow chart of acquisition of the signal detection method in the biophotonic measurement device of the present embodiment. In this view, a list of the signal detection methods is read (step S121). 1 is substituted for n (step S122). Measurement is executed based on the method n (step S123). Then, the quality of the measurement result is evaluated (step S124). Then, whether n is N or not is judged (step S125). If n is not N (No) in step S125, 1 is added to n (step S126), and step S123 is executed. If n is N (Yes) in step S125, the method with which the quality of the measurement result becomes the best is determined (step S127). Note that, herein, the embodiment in which the signal detection method is determined by utilizing the evaluation function values determined by the detection output of the photodetection units, in other words, the quality of measurement results has been described. However, furthermore, the signal detection method may be dynamically optimized in accordance with circumstances such as a human subject, part, task (cognitive task), etc.

Second Embodiment

Next, as a second embodiment, an embodiment about a method of determining an optimum intensity modulation frequency as the signal detection method of the combinations of the measurement points or the light sources and the detectors will be described. In the present embodiment, at the same time, in signal demodulation by a lock-in method such as the continuous light lock-in method as the signal detection method, automatic acquisition of optimum delay time, wherein the delay time of a reference signal subjected to multiplication of the detection signal, will be also described.

Figure 13:
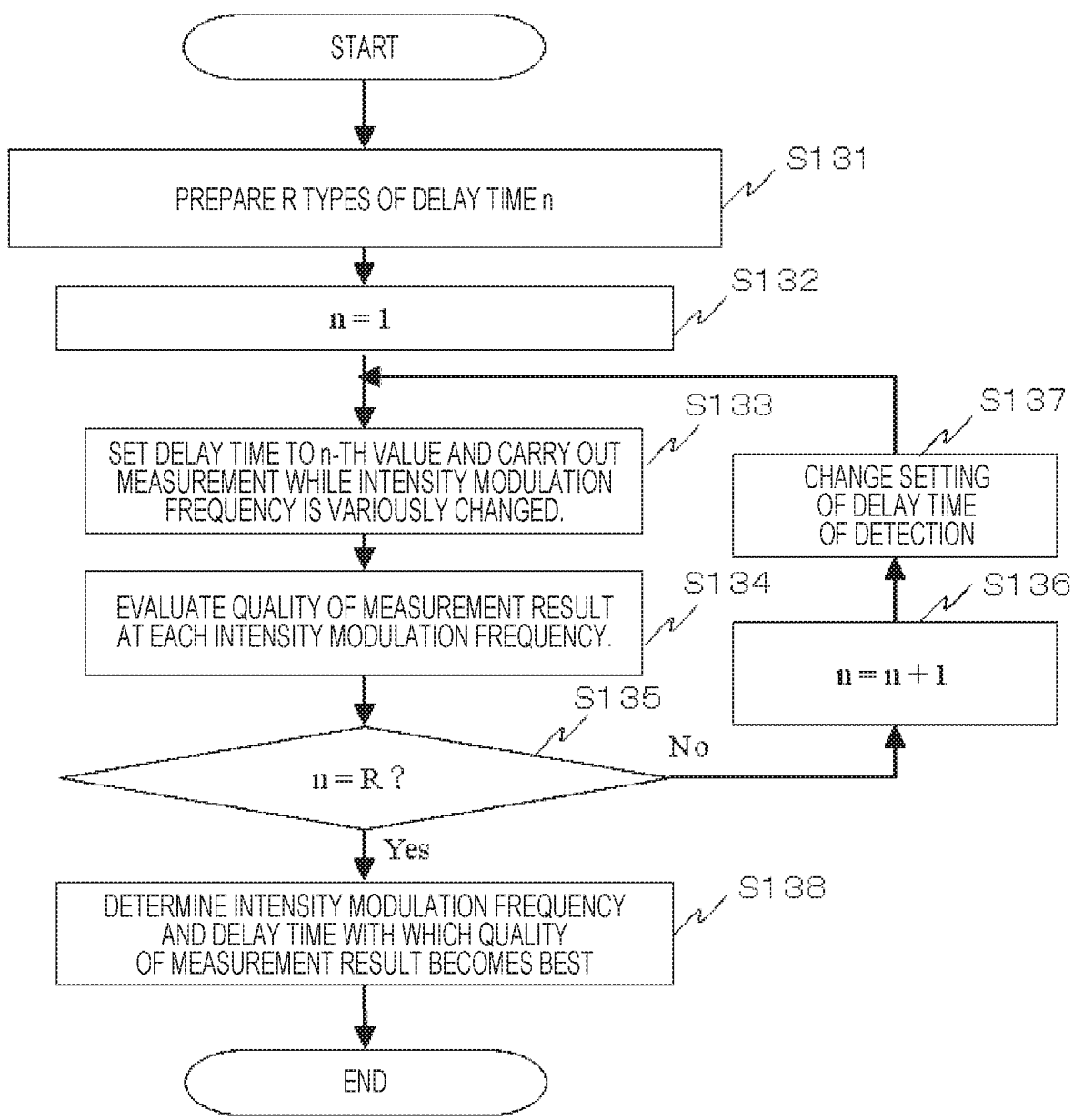
FIG. 13 shows a flow chart of a case of automatic acquisition of an optimum intensity modulation frequency and optimum delay time according to a second embodiment.

FIG. 13 shows a flow chart of automatic acquisition of an optimum intensity modulation frequency and optimum delay time. R types of delay time n are prepared (step S131). The delay time may be manually or automatically input from the input unit 107. Then, 1 is substituted for n (step S132). Among the R types of delay time, the n-th delay time is set for the reference signal of the lock-in of detection, and measurement is carried out while the intensity modulation frequency is variously changed (step S133). The quality of the measurement result at each of the intensity modulation frequencies is evaluated (step S134). Then, whether n is R or not is judged (step S135). If No in step S135, 1 is added to n (step S136), the setting of the delay time of detection is changed to the n-th value (step S137), and the process returns to step S133. If Yes in step S135, among the combinations of all the delay time and all the intensity modulation frequencies, the intensity modulation frequency and the delay time with which the quality of the measurement result becomes the best are determined (step S138). Note that, herein, the embodiment in which the optimum intensity modulation frequency and the optimum delay time are determined by utilizing the quality of the measurement results has been described. However, furthermore, the optimum intensity modulation frequency and the optimum delay time may be dynamically optimized in accordance with circumstances such as a human subject, part, task (cognitive task), etc.

Note that, in the present embodiment, the method of optimizing the intensity modulation frequency and the delay time has been described as the signal detection method. However, as the signal detection method, the precision or resolution (for example, 16 bits) of analog-to-digital (AD) conversion may be optimized in the detection system. If the AD conversion precision or resolution is enhanced, generally, a maximum sampling speed is reduced, and a bandwidth of the acquirable signal is affected. Furthermore, in a case in which the AD conversion is carried out in parallel with other CPU operations, the other CPU operations are also affected. Therefore, the AD conversion precision is not only required to be high, and the tradeoff of the influence to other systems has to be taken into consideration. Therefore, it is more desirable to cause the AD conversion precision to be included as one of the parameters for optimizing the signal detection method and then optimize the intensity modulation frequency and delay time.

Third Embodiment

Figure 14:
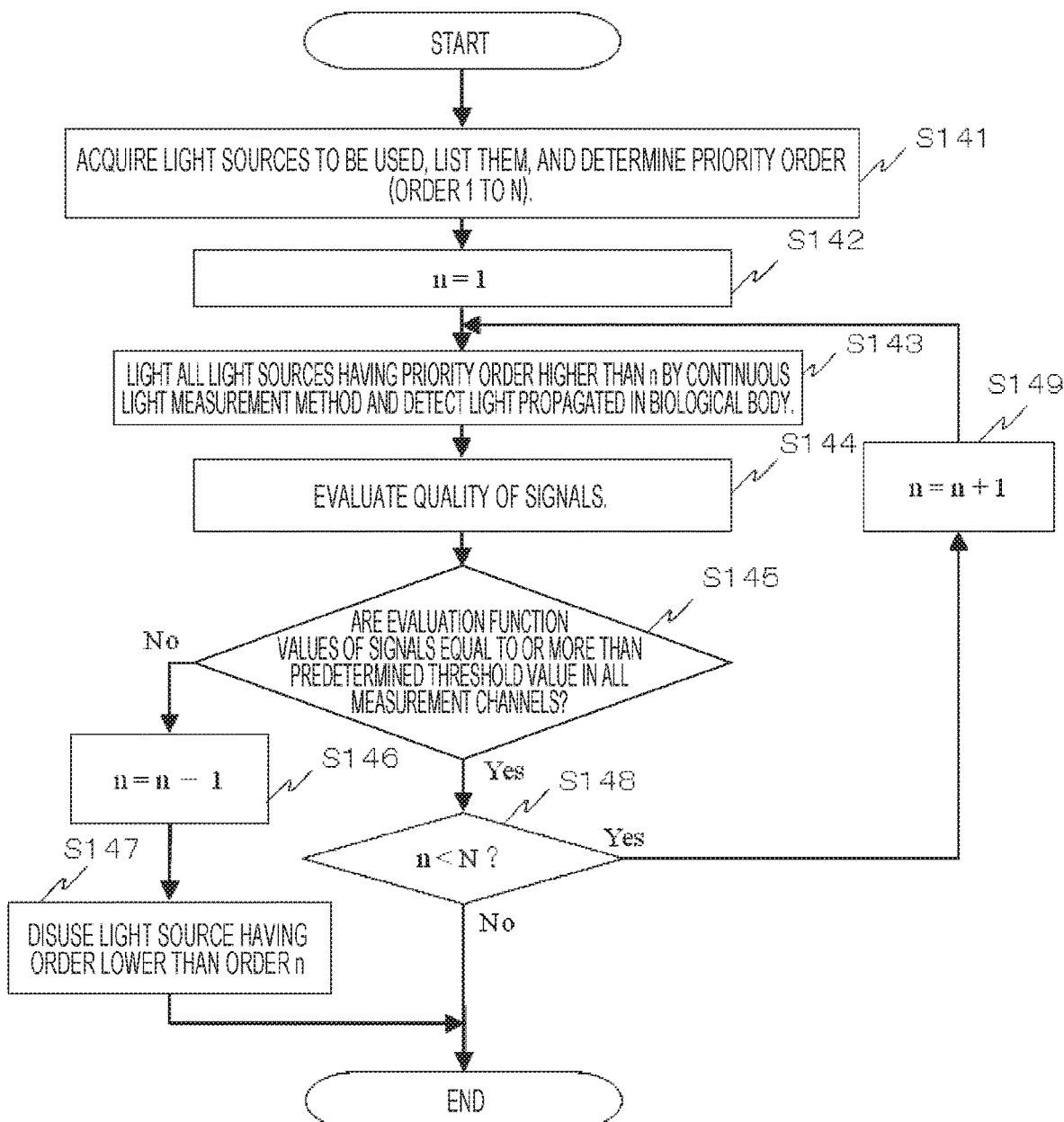
FIG. 14 shows a flow chart in a case of determination of the number of measurement channels according to quality evaluation of signals according to a third embodiment.

A third embodiment is an embodiment about a method of determining the number of measurement channels as the signal detection method by quality evaluation of measurement signals in the biophotonic measurement device. FIG. 14 shows a flow chart in a case of determination of the number of the measurement channels as the signal detection method by quality evaluation of the signals of the present embodiment. As shown in this view, first, the light sources to be used are acquired and listed, and a priority order thereof is determined (order 1 to N) (step S141). The order may be input in advance depending on the part and channel positions. Then, 1 is substituted for n (step S142).

The light source of the n-th priority order and all the light sources having the priority order higher than n are lit by the continuous light measurement method, and the light propagated in the biological body is detected (step S143). The quality of the detected signals is evaluated (step S144). Whether the evaluation functions of the signals are equal to or higher than a predetermined threshold value or not is judged in all the measurement channels (step S145). In step S145, if the number of the channels in which the evaluation function value is less than the predetermined threshold value is at least one (No), 1 is subtracted from n (step S146), and the light sources having the order lower than the order n is disused (step S147). In step S145, if the evaluation functions of the signals are equal to or higher than the predetermined threshold value in all the measurement channels (Yes), whether n is less than N or not is judged (step S148). In step S148, if n is less than N (Yes), 1 is added to n (step S149), and the process proceeds to step S143. In step S148, if n is equal to N (No), the process is terminated. In this case, N light sources are used.

As the quality of the signals in the biophotonic measurement device of the present embodiment, in addition to the carrier-to-noise ratio and the signal-to-noise ratio shown in Mathematical Expression 1 and Mathematical Expression 2 described above, the average value of detection-light-volume time-series data, the standard deviation of the detection-light-volume time-series data, etc. may be used.

Note that, herein, the method in which the light source is disused if the evaluation function value is less than the predetermined threshold value in the continuous lock-in method or the like which is the continuous light measurement method has been described. However, instead of discussing the light source, the method may be configured to switch to a time division method such as the time-division lock-in method so that the evaluation function value becomes equal to or higher than the predetermined threshold value.

Note that, herein, the example using light source systems as the photoirradiation modules and using photodetection and light reception systems as the photodetection modules has been described. However, a module may be configured to include both of the light source system and the light reception system, and a control module may be configured as a module which does not include both of the light source system and the light reception system and carries out only inter-module communication, etc.

Meanwhile, the correspondence acquiring unit may be configured to switch to the time division method or the time-division lock-in method simply in the case in which the number of the measurement points is equal to or higher than a predetermined number (for example, 6) with respect to one detection means. The threshold value of the number of measurement points depends on the quality of signals and is therefore changeable depending on measurement conditions. However, a rough indication may be determined according to laser safety standards (for example, IEC 60825) or the like, and optimization may be carried out according to actual measurement.

Fourth Embodiment

Figure 15:
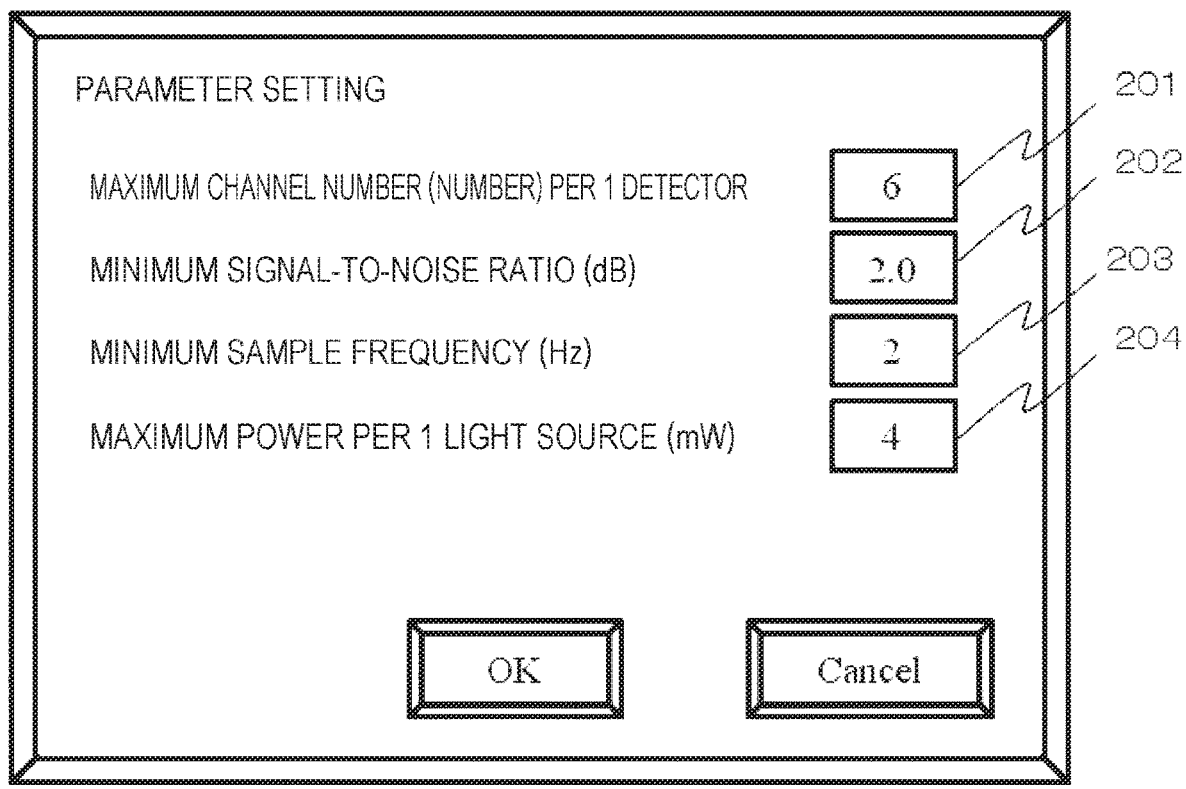
FIG. 15 is a view showing an example of the parameter setting screen of the biophotonic measurement device according to a fourth embodiment.

A fourth embodiment is an embodiment of a setting screen configuration of setting various parameters in the biophotonic measurement device. In the display unit 309 shown in FIG. 1 and FIG. 2, a setting screen of various parameters is presented so that a user can set various measurement parameters manually from the input unit 107. FIG. 15 is a view showing an example of the parameter setting screen of the present embodiment. The present screen displays a setting field 201 of a maximum channel number per a single detector, a setting field 202 of a minimum signal-to-noise ratio, a setting field 203 of a minimum sample frequency, and a setting field 204 of maximum photoirradiation power per a single light source; and setting values can be input from the input unit 107 and are determined by pressing an OK button of the setting screen after setting. When parameter setting is to be cancelled, a cancel button is pressed.

For example, as described before, when the signal-to-noise ratio is to be maximized, it is effective to, for example, reduce the number of channels and increase photoirradiation power. However, in the biophotonic measurement device of the present embodiment, the control/analysis unit 106 searches for optimum parameters while satisfying the conditions set herein. As a parameter search method of the biophotonic measurement device of the present embodiment, a full-number search method in which an optimum combination is searched for while all parameters are sequentially changed within changeable ranges, a method in which experimental parameter conditions are preferentially searched for, a method in which parameter conditions are randomly changed, etc. may be set depending on the limitation of search time. Note that, in preparation for a case in which a plurality of parameter conditions that satisfies limiting conditions are present, it can be configured so that the parameter(s) to be prioritized can be set in advance.

Hereinabove, various preferred embodiments of the present invention have been described. However, the present invention is not limited to the above described embodiments and includes various modification examples. For example, as a different means of the correspondence acquiring unit 19 of FIG. 2, the correspondence relations of the light sources, which are the photoirradiation unit, and the photodetectors, which are the photodetection units, may be automatically acquired by providing a position identifying unit which identifies the photoirradiation points, which are the positions to be subjected to photoirradiation on the subject 10, and the positions of the detection points, which are the positions to detect the light on the subject. In such a configuration, without the need to worry about the order of inserting fibers or probes into probe holders or about IDs and numbers of the probes, arbitrary light-source fibers can be inserted to the probe holders for the light sources, arbitrary light-detection fibers can be inserted to the probe holders for the photodetectors, and there is an effect that measurement preparation can be carried out fast. Since photodetection methods can be automatically acquired, hardware setting can be flexibly changed to carry out measurement. Meanwhile, if conditions are not changed among human subjects, the setting can be fixed. The position identifying unit like this may be a magnetic sensor, a camera, or the like. If a magnetic sensor is to be used as the position identifying unit, 3-dimensional position measurement is enabled by installing a magnetic transmitter outside the device, attaching magnetic sensors to the individual optical device modules, and detecting outputs of the magnetic sensors.

Fifth Embodiment

In addition to the above described embodiments, the biophotonic measurement device of the present invention may be configured to be characterized by having electronic circuits and elements including resistances serving as backups, condensers (capacitors), analog ICs, etc., is capable of switching use/disuse of each element, and switches use/disuse of each element so as to appropriately maximize the evaluation function value. More specifically, the parameters of the switchable signal detection methods include the time-division lock-in detection method, the continuous lock-in detection method, etc.; signal feature amounts such as intensity modulation frequencies; and hardware configurations such as the combinations of used elements. These can be used also for optimization of the quality of signals, and, as a backup of the element, the element can function as a replacement of a failed element.

According to the present invention described above, in biological-body measurement devices which can be used as medical and research equipment or can be used for checking educational effects and rehabilitation effects, health management at home, market researches such as commercial-product monitoring, and tissue oxygen-saturation-degree measurement or oxygen metabolism measurement of muscles by similar methods, highly reliable signals can be provided by dynamically changing optimum device configurations and improving the quality of signals.

Note that the present invention is not limited to the above described embodiments, but includes various modification examples. For example, the above described embodiments have been described in detail for better understanding of the present invention, and the present invention is not necessarily limited to be provided with all the configurations of the description. Moreover, part of the configuration of a certain embodiment can be replaced by the configuration of another embodiment. Moreover, to the configuration of a certain embodiment, the configuration of another embodiment can be added. Also, part of the configurations of the embodiments can be subjected to addition/deletion/replacement of the other configurations. For example, the above described embodiments have been described on the assumption that the photodetection methods are selected for the measurement channels. However, if a plurality of wavelengths is used in a single measurement channel, the evaluation function values may be maximized so that different methods may be employed among the wavelengths. More specifically, when it is assumed that hemoglobin changes are calculated by using 3 types of wavelengths at a single measurement point or measurement channel, a setting in which a wavelength 1 uses the continuous lock-in method and wavelengths 2 and 3 use the time-division lock-in method can be used.

Furthermore, the case in which the above described configurations, functions, control/analysis unit, etc. are realized by software by creating a program which realizes part or all thereof has been described as an example. However, it goes without saying that part or all thereof may be realized by hardware, for example, by designing by integrated circuits.

In the disclosure of the present description described above in detail, various inventions are disclosed in addition to the invention described in claims. Part of them is listed below.

[List 1]

A biophotonic measurement device including:

one or a plurality of photoirradiation units for radiating light to a predetermined photoirradiation point;

one or a plurality of photodetection units for detecting the light, which is radiated from the photoirradiation unit, at a predetermined photodetection point; and one or a plurality of optical device modules for storing at least one of the photoirradiation unit and the photodetection unit, wherein signal detection methods can be switched among each of the optical device modules, and the plurality of signal detection methods is mixable at measurement points.

[List 2]

The biophotonic measurement device according to list 1, including a correspondence acquiring unit for acquiring a correspondence relation between each of the photodetection unit and the photoirradiation unit predetermined, which is an irradiation source of the light detected by the photodetection unit, wherein the correspondence relation and the evaluation function value determined by detection intensity of the photodetection unit or by the detection intensity and a measurement condition are utilized.

[List 3]

The biophotonic measurement device according to list 1, wherein the optical device module includes:

an information storage unit storing information about at least one of the photoirradiation unit and the photodetection unit; and a control communication unit for controlling at least one of the photoirradiation unit and the photodetection unit and communicating with the other optical device module.

[List 4]

The biophotonic measurement device according to list 1, including a position identifying unit configured to identify positions of a photoirradiation point, which is a position on the subject subjected to photoirradiation by the photoirradiation unit, and a detection point, which is a position on the subject subjected to detection of light by the photodetection unit.

[List 5]

The biophotonic measurement device according to list 1, wherein the information storage unit retains a wavelength and current-light output characteristics of the photoirradiation unit and retains sensitivity information of the photodetection unit.

[List 6]

The biophotonic measurement device according to list 1, wherein the correspondence relation is a combination of the photoirradiation unit predetermined and the photodetection unit which detects the light radiated by the predetermined photoirradiation unit is a SD distance defined by a distance between the irradiation point and the detection point.

[List 7]

The biophotonic measurement device according to list 1, wherein the correspondence acquiring unit acquires a combination of a time-average detection light volume or a signal-to-noise ratio of a case in which measurement is carried out with the optical device module installed on the subject or a standard phantom.

[List 8]

The biophotonic measurement device according to list 1, wherein the signal detection method includes setting of precision of AD conversion of carrying out analog/digital conversion of the detection output of the photodetection unit.

[List 9]

The biophotonic measurement device according to list 1, wherein when the signal detection method is a lock-in method, delay time of detection in the signal detection method is optimally set based on the evaluation function value.

[List 10]

The biophotonic measurement device according to list 1, wherein an intensity modulation frequency of a light source of the photoirradiation unit is optimally set based on the evaluation function value.

REFERENCE SIGNS LIST 10 human subject
11 irradiation point
12 detection point
13, 23 photoirradiation module
14, 24 photodetection module
15 communication unit
16 information storage unit
17 control communication unit
18 central control/analysis unit
19 correspondence acquiring unit
20 device main body
21 control module
22 inter-module communication bus
25 communication bus between module and information terminal
26 information terminal
30 light
31 CPU and storage unit
32 module information
33 module ID
34 inter-module connector
35 firmware-writing connector
36 amplifier
37 inter-module communication connector
38 connector for communication with information terminal
39 power source
40 waveguide
41 substrate
42 light-source position
43 photodetector position
44, 45, 46 probe holder
50 combination for carrying out continuous light lock-in measurement
51 combination for carrying out quasi continuous light lock-in measurement
52 combination for carrying out time-division lock-in measurement
61 photodetection waveforms (ch 1, 2) of continuous light lock-in method
62 photodetection waveform of quasi continuous light lock-in method
63 photodetection waveforms (ch 1 to 3) of time-division lock-in method
64 photodetection waveforms (ch 1, 2) of lock-in switch method
65 photodetection waveforms (ch 1 to 3) of time-division detection method
101 light source
102 photodetector
103 light-source driving device
104 amplifier
105 analog-to-digital converter
106 control/analysis unit
107 input unit
108 storage unit
109 display unit
201 setting field of maximum channel number per single detector
202 setting field of minimum signal-to-noise ratio
203 setting field of minimum sample frequency
204 setting field of maximum photoirradiation power per single light source

The invention claimed is:

1. A biophotonic measurement device comprising:
a plurality of light sources configured to radiate light to a plurality of respective photoirradiation points;
a photodetector configured to detect the light, which is radiated from the light sources, at a photodetection point; and
a processing unit configured to control the light sources and the photodetector according to two or more signal detection methods,
wherein the processing unit is further configured, for each of the signal detection methods, to:
control the plurality of light sources to sequentially radiate the light to the respective photoirradiation points,
measure the light from each of the light sources detected by the photodetector according to the respective signal detection method,
calculate a plurality of evaluation function values which correspond to the measured light from each of the light sources according to the respective signal detection method,
determine the light sources which have the evaluation function values equal to or greater than a predetermined threshold value for the respective signal detection method, and
set, for each of the light sources having one of the evaluation function values which is equal to or greater than a predetermined threshold value, the respective light source and the photodetector as a respective channel for the respective signal detection method.

2. The biophotonic measurement device according to claim 1, wherein
the processing unit is further configured, for each of the signal detection methods, to:
calculate the evaluation function values using intensities of the measured light from each of the light sources.

3. The biophotonic measurement device according to claim 1, wherein
the signal detection methods include at least one of a continuous light lock-in method, a quasi continuous light lock-in method, a time-division detection method, a time-division lock-in method, and a code division modulation method.

4. The biophotonic measurement device according to claim 3, wherein
the processing unit is further configured to:
upon setting a predetermined number or more of respective channels for the continuous light lock-in method or the quasi continuous light lock-in method, select the time-division detection method or the time-division lock-in method as the signal detection method for measurement of a subject.

5. The biophotonic measurement device according to claim 1, wherein
the processing unit is further configured, for at least one of the signal detection methods, to:

set a plurality of delay times,
measure, for each of the delay times, the light from each of the light sources detected by the photodetector according to the respective at least one of the signal detection method while the light is varied at a plurality of intensity modulation frequencies,
calculate, for each of the delay times, the plurality of evaluation function values which correspond to the measured light from each of the light sources at each of the intensity modulation frequencies, and
determine an optimum intensity modulation frequency and an optimum delay time based on the evaluation function values for each of the delay times and each of the intensity modulation frequencies.

6. The biophotonic measurement device according to claim 5, wherein
the delay times are delay times of a reference signal of signal demodulation.

7. The biophotonic measurement device according to claim 1, wherein
the processing unit is further configured, for each of the signal detection methods, to:
set a precision of analog/digital conversion of the detected light measured by the photodetector.

8. The biophotonic measurement device according to claim 1, further comprising:
a plurality of optical device modules in which the plurality of light sources and the photodetector are arranged,
wherein each of the optical device modules includes:
an information storage unit storing information about the one of the light sources or the photodetector arranged therein; and
a control communication unit for controlling communication with the other optical device modules.

9. The biophotonic measurement device according to claim 8, wherein
the information storage unit stores a wavelength and current-light output characteristics of the one of the light sources arranged therein or sensitivity information of the photodetector arranged therein.

10. The biophotonic measurement device according to claim 8, wherein
the processing unit calculates a time-average detection light volume or a signal-to-noise ratio as the evaluation functions which correspond to the measured light from each of the light sources when measurement is carried out with the optical device modules installed for a subject or a standard phantom.

11. The biophotonic measurement device according to claim 8, wherein
each of the optical device modules includes a magnetic sensor configured to identify a position of the photoirradiation point or of the photodetection point.

12. A biophotonic measurement method of a biophotonic measurement device including a plurality of light sources configured to radiate light to a plurality of respective photoirradiation points, and a photodetector configured to detect the light, which is radiated from the light sources, at a photodetection point, the biophotonic measurement method comprising:
controlling, for each of two or more signal detection methods, the plurality of light sources to sequentially radiate the light to the respective photoirradiation points;
measuring the light from each of the light sources detected by the photodetector according to the respective signal detection method;
calculating a plurality of evaluation function values which correspond to the measured light from each of the light sources according to the respective signal detection method;
determining the light sources which have the evaluation function values equal to or greater than a predetermined threshold value for the respective signal detection method; and
setting, for each of the light sources having one of the evaluation function values which is equal to or greater than a predetermined threshold value, the respective light source and the photodetector as a respective channel for the respective signal detection method.

13. The biophotonic measurement method according to claim 12, wherein
a predetermined distance is set between each of the photoirradiation points and the photodetection point.

14. The biophotonic measurement method according to claim 12, wherein
the evaluation function values are calculated by using intensities of the measured light from the photodetector.

15. The biophotonic measurement method according to claim 12, wherein
the signal detection methods include at least one of a continuous light lock-in method, a quasi continuous light lock-in method, a time-division detection method, a time-division lock-in method, and a code division modulation method.

16. The biophotonic measurement method according to claim 15, further comprising:
upon setting a predetermined number or more of respective channels for the continuous light lock-in method or the quasi continuous light lock-in method, selecting the time-division detection method or the time-division lock-in method as the signal detection method for measurement of a subject.

17. The biophotonic measurement method according to claim 12, further comprising:
setting, for at least one of the signal detection methods, a plurality of delay times;
measuring, for each of the delay times, the light from each of the light sources detected by the photodetector according to the respective at least one of the signal detection method while the light is varied at a plurality of intensity modulation frequencies;
calculating, for each of the delay times, the plurality of evaluation function values which correspond to the measured light from each of the light sources at each of the intensity modulation frequencies; and
determining an optimum intensity modulation frequency and an optimum delay time based on the evaluation function values for each of the delay times and each of the intensity modulation frequencies.

* * * * *